US005587520A

United States Patent [19]
Rhodes

[11] Patent Number: 5,587,520
[45] Date of Patent: Dec. 24, 1996

[54] THERMAL CONDUCTIVITY DETECTOR

[75] Inventor: Robert P. Rhodes, Lincoln University, Pa.

[73] Assignee: Hewlett-Packard Company, Palo Alto, Calif.

[21] Appl. No.: 537,182

[22] Filed: Sep. 29, 1995

[51] Int. Cl.$^6$ ..................................................... G01N 25/18
[52] U.S. Cl. ................... 73/25.03; 73/202.5; 73/204.11; 73/204.15
[58] Field of Search ................................. 73/25.03, 35.05, 73/202.05, 204.11, 204.15

[56] References Cited

U.S. PATENT DOCUMENTS

| | | | |
|---|---|---|---|
| 1,224,321 | 5/1917 | Phillip et al. | 73/25.03 |
| 2,116,239 | 5/1938 | Heblerr | 73/25.03 |
| 4,088,458 | 5/1978 | Jourdan | 55/197 |
| 4,100,790 | 8/1978 | Harvey | 73/23.1 |
| 4,185,490 | 1/1980 | Clouser et al. | 73/23.1 |
| 4,215,564 | 8/1980 | Lawson et al. | 73/27 R |
| 4,254,654 | 3/1981 | Clouser et al. | 73/27 R |
| 4,461,166 | 7/1984 | Gatten et al. | 73/27 R |
| 4,735,082 | 4/1988 | Kolloff | 73/27 R |
| 4,741,198 | 5/1988 | Farren et al. | 73/23.1 |
| 5,265,459 | 11/1993 | Cohen | 73/25.03 |
| 5,342,580 | 8/1994 | Brenner | 422/92 |
| 5,379,630 | 1/1995 | Lacey. | |
| 5,473,162 | 12/1995 | Busch et al. | 250/341.6 |

*Primary Examiner*—Hezron E. Williams
*Assistant Examiner*—Jay L. Politzer
*Attorney, Agent, or Firm*—Mark Z Dudley

[57] ABSTRACT

A thermal conductivity detector includes a cavity wall defining a cavity for receiving a quantity of the sample fluid, the cavity wall being subject to a cavity wall temperature, and a sensor located in the cavity and connected as a first element in a bridge circuit configuration. The sensor exhibits a resistance which is dependent on a temperature of the sensor. A variable resistor having a selectable resistance in response to a control signal is connected in the bridge circuit configuration as a second element. A signal providing means, connected to the balance nodes of the bridge circuit configuration, provides a first signal which is related to a change in resistance of the sensor and thereby representative of the sensor temperature. Means for sensing the temperature of the cavity wall provides a temperature sense signal to a controller, which in response provides a heating control signal to a cavity wall heating means. The controller also determines the cavity wall temperature and in response causes the variable resistor to achieve a selected resistance value that will cause the sensor resistance to change. The temperature of the sensor is thereby set so as to accurately and reliably establish a selectable, predetermined temperature differential between the sensor and the cavity wall.

7 Claims, 2 Drawing Sheets

THERMAL CONDUCTIVITY DETECTOR

FIELD OF THE INVENTION

This invention relates to thermal conductivity measurement devices, and in particular, to precision measurement devices for measuring the thermal conductivity of a fluid, such as a gas, to detect compounds within the fluid.

BACKGROUND OF THE INVENTION

Gas chromatographs are used to determine the chemical composition of a sample, which may be gaseous or a vaporized liquid. The term gas will hereinafter be used to include a vapor. In one type of gas chromatograph, a sample is sent through a separation column. A typical separation column is a long capillary tube with a coated interior. Different chemical compounds in the sample travel through the separation column at different rates and leave the separation column at different times. As compounds leave the separation column, they are carried by a carrier gas past a detector. The detector detects compounds in the carrier gas by measuring changes in the properties of the effluent gas. When a change in the gas property occurs, the timing of the change indicates the type of the compound passing the detector, and the magnitude of the change indicates the quantity of the compound.

One type of detector used with gas chromatographs is a thermal conductivity detector, which detects changes in the thermal conductivity of the effluent gas. When a compound is mixed with the carrier gas, the thermal conductivity of the mixture is usually different from that of the pure carrier gas. A thermal conductivity detector provides a measure of the change in the thermal conductivity of the carrier gas and thereby provides a measure of the presence and amount of various compounds.

FIG. 1 shows a typical prior art sensor circuit 10 used in a thermal conductivity detector of a gas chromatograph. The sensor circuit 10 includes a metal filament 22, such as a platinum wire, placed in a wall 18 of a cavity 24. The effluent from a gas separation column along with a carrier gas fills the cavity 24 and flows past the filament 22. The filament 22 has a resistance $R_S$ which depends on its temperature and is heated using an electric current $I_2$. In the case of the filament 22 being a platinum wire, the resistance of the filament 22 is proportional to its temperature.

Heat generated by the filament 22 is removed partially by the flow of the effluent but primarily by thermal conduction through the gas to the walls 18 of the cavity 24, thus lowering the resistance of the filament 22. By effectively measuring the change in resistance of the heated filament 22, the change in thermal conductivity of the flowing gas may be determined.

In some applications, problems arise that can cause the output of a detector to change even if the composition of the gas remains constant. One problem is caused by changes in the temperature of the walls 18 of the cavity 24. Another problem is caused by changes in the temperature of the carrier gas. Another problem is electronic drift of the energizing voltage which controls the current through the filament 22. With the sensitivity required of a detector, even thermoelectric potentials generated in electrical connections may affect the detector. Changes in the voltage offset of the amplifiers used to measure changes in the resistance of filament 22 are still another problem.

Thus, one of the problems encountered with such detectors is that the heat flow between the filament and the cavity wall 18 of the cavity 24 is directly affected by the temperature of the cavity wall 18. For this reason it has been customary to reduce the effect of ambient temperatures on the temperature of the cavity wall 18 by imbedding the cavity 24 in a heated block 14. A temperature control circuit (not shown) is employed to heat the block to an elevated temperature, such as approximately 150 to 250 degrees C. The block temperature is typically selected by the user according to the requirements of the particular type of analysis being performed.

The filament 22 is operated in a bridge circuit employing an embedded resistor 12 that is typically a platinum resistance type (PRT) sensor and is located in the cavity wall 18 of cavity 24. Resistors $R_b$ and $R_a$ have fixed resistance values and are chosen to give the desired resistance in filament 22 when the bridge circuit is balanced. A differential amplifier 26 detects an unbalance in the bridge. A DC voltage ($V_A$) is used to heat the filament 22 to a temperature typically between 40 degree(s) to 100 degree(s) C. above the temperature of the cavity wall 18 in accordance with balanced operation of the bridge circuit. If the thermal conductivity of the effluent in the cavity 24 is different from that of a pure carrier gas in cavity 24, the bridge becomes unbalanced, and a change in the amplifier's output voltage $V_A$ indicates the detection of a change in thermal conductivity of the gas in the cavity 24. A variation in the wall temperature of the cavity 24 will change the resistance of the embedded resistor 12 and thus alter the balance point of the bridge circuit. The power supplied to filament 22 thereby changes, thus altering the temperature of the filament 22 to compensate for the effects of a variation in the cavity wall temperature.

If the temperature of the filament 22 is not set to exceed the temperature of the cavity wall 18 by a sufficient temperature differential, the sensitivity of the sensor circuit 10 suffers and the output signal $V_A$ may be subject to the effects of noise signals. If the temperature differential is too large, then the filament 22 expands and may no longer be kept under tension. The output signal $V_A$ may then be subject to the effects of noise signals and the filament 22 is subject to destructive contact with the cavity wall 18. It would be advantageous, therefore, to provide a thermal conductivity detector that provides an appropriate temperature differential in an automatic, accurate, and reliable fashion.

Another problem is that the embedded resistor 12 offers less than satisfactory performance in some applications. The resistance or temperature coefficient of the embedded resistor 12 may change with time, thus causing an undesirable shift in the temperature differential between the temperature of the cell wall 18 and the temperature of the filament 22. The embedded resistor 12 is expensive, and must be carefully and properly embedded in the block 14, thus increasing manufacturing costs. The embedded resistor 12 also presents a problem in that its leads must be directed out of the block 14 so as to be attached to the appropriate connections in the sensor circuit 10. These leads are prone to failure because they are fragile and the insulation material on the leads is subject to degradation at the elevated temperatures of the block 14 when heated. The insulation can fail and cause a short circuit between a lead and the block 14. A further problem occurs when the leads from the embedded resistor 12 are accidentally confused with the leads from the filament 22 during assembly of the circuit 10. The resulting connections can allow misdirection of current in the circuit 10, thus damaging certain components in the circuit.

Accordingly, an improved sensing circuit and method of operation for detecting thermal conductivity are needed to avoid the problems associated with the embedded resistor 12 in a bridge type sensor circuit 10.

SUMMARY OF THE INVENTION

A thermal conductivity detector may be constructed according to the present invention to include a cavity wall defining a cavity for receiving a quantity of the sample fluid, the cavity wall being subject to a cavity wall temperature, and a sensor located in the cavity and connected as a first element in a bridge circuit configuration. The sensor exhibits a resistance which is dependent on a temperature of the sensor. A variable resistor having a selectable resistance in response to a control signal is connected in the bridge circuit configuration as a second element. A signal providing means, connected to the balance nodes of the bridge circuit configuration, provides a first signal which is related to a change in power delivered to the sensor and thereby representative of the thermal conductivity of the sample fluid. Means for sensing the temperature of the cavity wall provides a temperature sense signal to a controller, which in response provides a heating control signal to a cavity wall heating means. The controller also determines the cavity wall temperature and in response causes the variable resistor to achieve a selected resistance value that will cause the sensor resistance to change. The temperature of the sensor is thereby set so as to accurately and reliably establish a selectable, predetermined temperature differential between the sensor and the cavity wall.

DETAILED DESCRIPTION OF THE PREFERRED EMBODIMENTS

Figure 1:
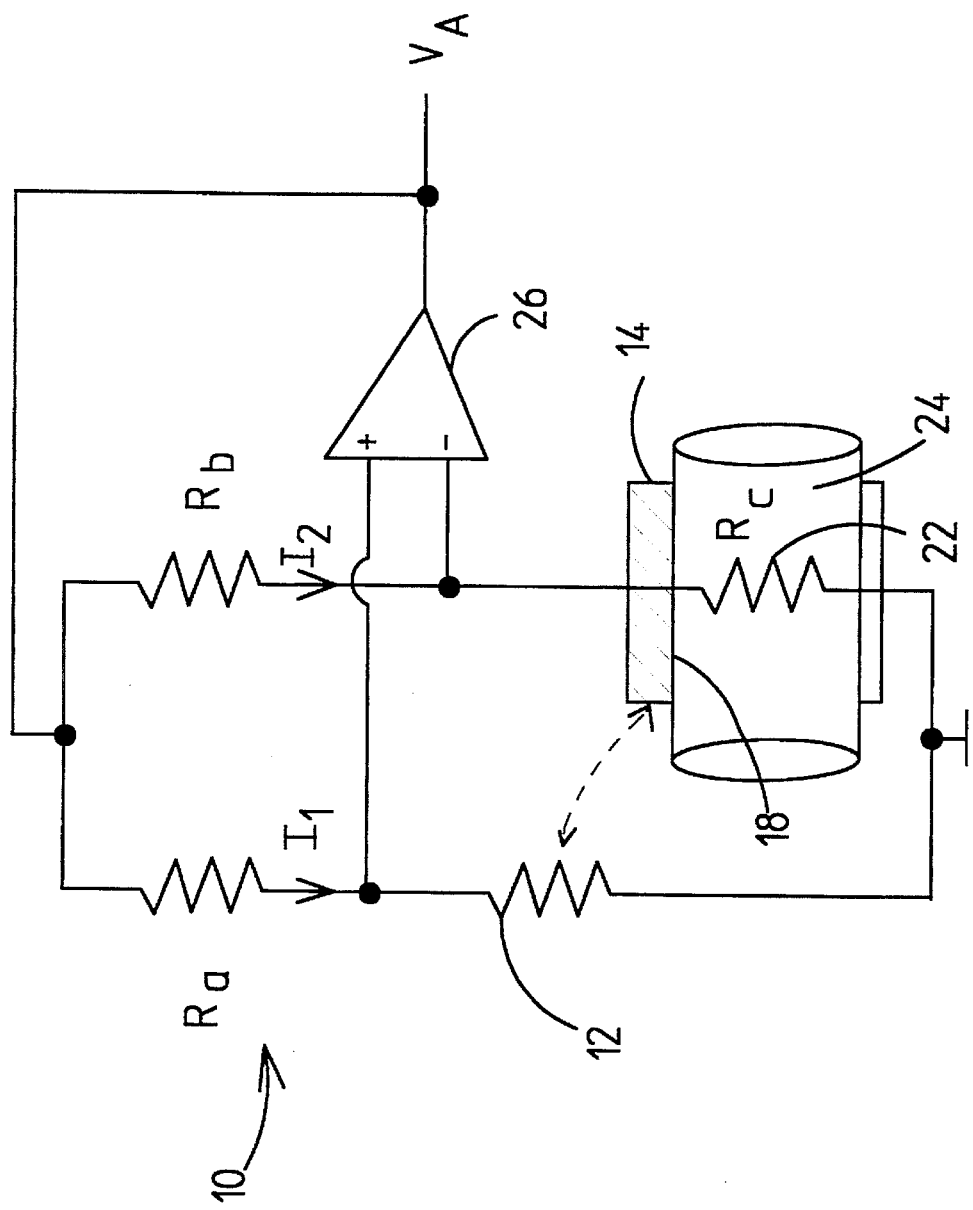
FIG. 1 is a schematic diagram of a prior art thermal conductivity detector.

The apparatus and methods of the present invention provide improved accuracy in a thermal conductivity detector suitable for use in an analytical instrument. The terms "analysis" and "analytical" are meant broadly to include both qualitative and quantitative analytical methods, detection, or observation of physical or chemical parameters. Additionally, the apparatus and methods described herein may be applied to directly or indirectly effect selective temperature control of a heated resistive element that may be present within a heated zone or cavity in an analytical instrument.

Chromatographic analysis of gaseous sample is the preferred mode of analysis according to the practice of the present invention, and the following description of the invention will be directed to a thermal conductivity detector intended for use in a gas chromatographic analytical system. However, the teachings herein may be applied to a thermal conductivity detector suitable for use in an analytical instrument for effecting a chromatographic analysis of multiple component gases and mixtures thereof capable of regulated flow. Moreover, it should be understood that the teachings herein are applicable to such a detector for use in instruments that operate using other analytical methods or that analyze or detect other physical parameters and phenomena.

The basic mechanism underlying chromatographic analysis is the separation of a sample chemical mixture into individual components by transporting the mixture in a carrier fluid through a specially prepared separation column having a retentive media therein. The carrier fluid is referred to as the mobile phase and the retentive media is referred to as the stationary phase. The principal difference between liquid and gas chromatography is that the mobile phase is either a liquid or a gas, respectively. Liquid chromatography devices are capable of analyzing much heavier compounds than gas chromatography devices. However, gas chromatography detection techniques are more sensitive and therefore the present invention contemplates the use of a gas chromatographic method, although for the purposes of clarity, only the detector portion of the gas chromatograph is illustrated.

In a gas chromatographic analysis, an inert carrier gas is passed through a temperature-controlled column which contains a stationary phase in the form of porous sorptive media, or through a hollow capillary tube having an inner diameter coated with the stationary phase. A sample of the subject mixture is injected into the carrier gas stream and passed through the column. Separation is due primarily to differences in the partial pressures of each sample component in the stationary phase versus the mobile phase. These differences are a function of the temperature within the column. As the basic techniques for the preparation, separation, and detection of sample components are known to those skilled in the art, the description to follow will be directed primarily to the temperature control of a heated filament in a thermal conductivity detector. Thus, the following description illustrates a single cell thermal conductivity detector that is accurate, reliable, inexpensive, and capable of attaining accurate readings within minutes after power is applied to the filament.

Figure 2:
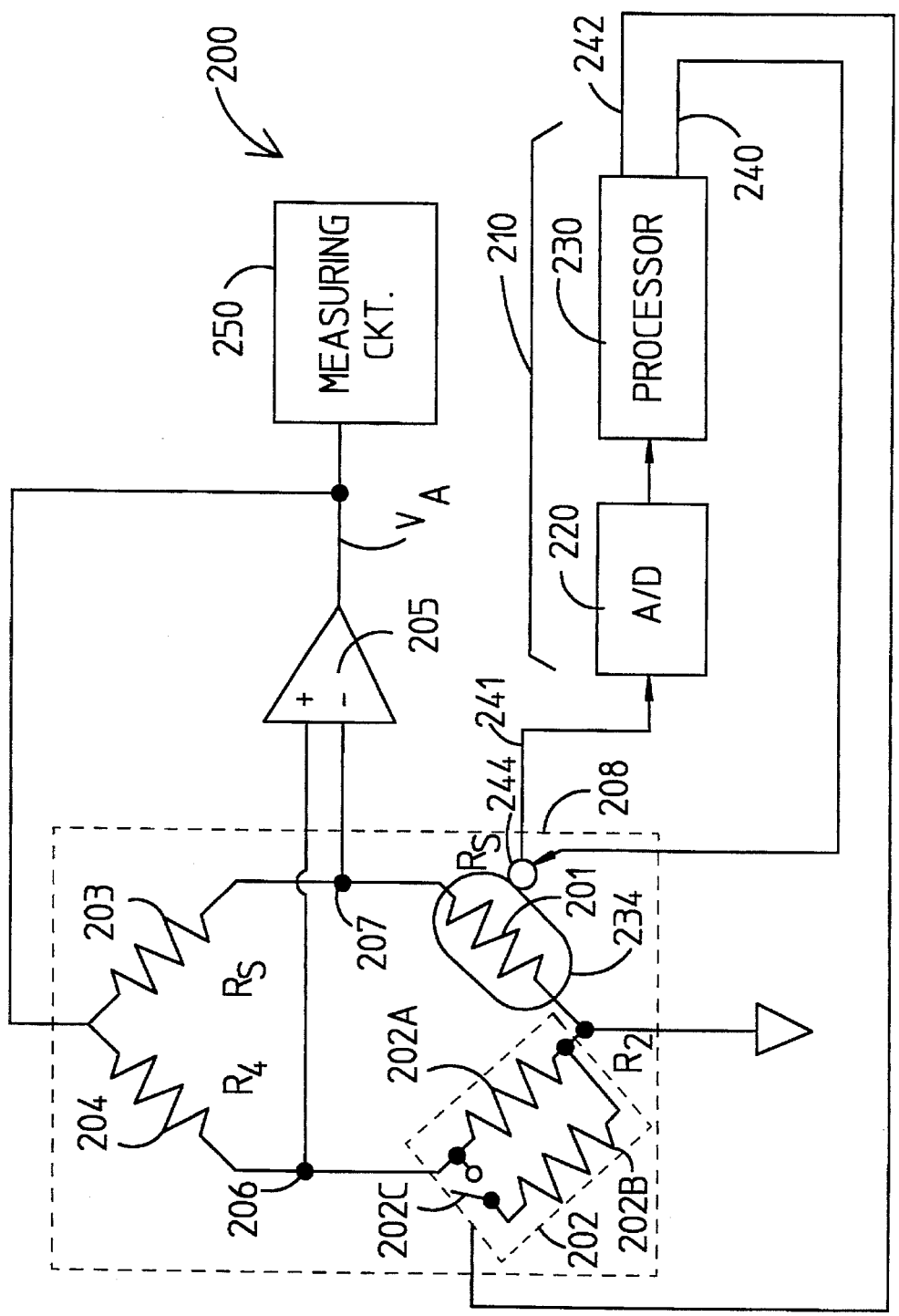
FIG. 2 is a simplified schematic diagram of a thermal conductivity detector constructed according to the present invention.

In the thermal conductivity detector 200 schematically illustrated in FIG. 2, a reference gas or the elutant from a column in a chromatograph are provided to a cavity 234 in a thermal conductivity cell in a switched manner which need not be presented, as it is known in the art and not part of this invention. The teachings herein comprehend the use of, for example, known techniques for subjecting the filament in a thermal conductivity detector to modulated fluid flow, as disclosed in U.S. Pat. No. 4,254,654, filed on Oct. 7, 1976, and entitled "Modulated Fluid Detector", the disclosure of which is incorporated herein by reference. The wall of the cavity 234 has a temperature which may be programmed in a manner known in the art by, for example, a programmed controller 210 which receives a temperature sense signal (representative of the temperature of the wall of cavity 234) and provides a heating control signal on line 240 to a combination temperature sensing and heating unit 244. (Other means, such as controllable vents, may also be used to control temperature.) The gas flow in the cavity 234 is switched at a given frequency from the output of the column to a source of reference gas so that its output signal, i.e., the voltage required to keep the sensor 201 at a given temperature, varies between a value determined by the thermal conductivity of the gas eluting from the column and a value determined by the thermal conductivity of the reference gas. The switching frequency is such that a number of switching cycles occur during the elution of each peak of sample gas from the column.

In a particular feature of the present invention, and as illustrated in FIG. 2, a preferred embodiment of a thermal conductivity detector 200 may be constructed to include a sensor 201 that is controlled to operate at a selected one of a plurality of differing sensor temperatures. The sensor 201 may take the form of the filament 22 shown in FIG. 1 and described above. The gas having a thermal conductivity that is to be measured flows through the cavity 234 as described hereinabove. The sensor 201 is connected to resistors 202, 203, and 204 in a bridge circuit 208. The resistor 202 is a variable resistor which changes its resistance according to a variable resistance characteristic, such as by the connection or disconnection of a plurality of fixed resistors 202A, 202B via a controllable switch 202C. By way of a control signal provided by a controller 210 on a control signal line 242, the switch 202C may be opened, whereupon the resistor 202 assumes the resistance of resistor 202A. When the switch 202C is closed, the resistor 202 assumes the resistance of resistors 202A and 202B connected in parallel. In the preferred embodiment, the controller 210 includes an analog to digital (N/D) converter 220 and a processor 230.

As will be appreciated by those skilled in the art, any type of resistor that is responsive to a control signal and capable of having at least two selectable resistances may be employed in place of the variable resistor 202. In particular, the resistor 202 may be provided in a form that offers more than two selectable resistance values. The resistor 202 may thus include an electromechanical switch such as a relay; discrete analog or digital switching devices; analog circuits that provide a selectable impedance, such as a linear operational amplifier; or discrete or integrated logic devices, as will be appreciated by those skilled in the art in accordance with the teachings herein. In contrast to the prior art, the resistors 202–204 can be located remote from the cavity 234, on (for example) a conventional circuit board assembly along with the controller 210. None of the resistors 202–204 need to be imbedded or otherwise integrated with the wall of cavity 234.

A differential amplifier 205 has input terminals connected to balance nodes 206 and 207. The amplifier 205 has an output terminal connected to the common node of resistors 203 and 204 so that the amplifier 205 acts as a variable power supply for dynamically balancing the bridge 208. The output of the amplifier 205 is also connected to a measuring circuit 250, which receives an output voltage $V_A$ of the amplifier 205 and measures the power dissipation changes in the bridge 208 based upon the value of the output voltage $V_A$ at various times. This change in power dissipation is then used to calculate the thermal conductivity of a sample. The detected level of one or more analytes in the sample may then be indicated on an information output device (not shown). Suitable information output devices are known in the art and may include a strip chart recorder, a segmented or alphanumeric character display, a video display, or audio frequency transducer.

In the embodiment shown in FIG. 2, the resistances $R_2$, $R_3$, and $R_4$ of the resistors 202, 203, and 204, respectively, determine the resistance $R_S$ of the sensor 201 necessary to balance the bridge 208. If $R_3$ and $R_4$ are equal then $R_S$ must equal $R_2$ to balance the bridge.

In operation, the processor 230 is operated according to techniques known in the art to effect a selected one of a plurality of desired cavity wall temperatures by control of the combined temperature sensing and heating unit 244 that is preferably integral with the wall of the cavity 234. In a particular feature of the present invention, the temperature of the sensor 201 is also adjusted to a selectable, appropriate value by switching the resistance of the resistor 202 to a selected one of a plurality of resistance values, whereupon the value of the voltage $V_A$ is self-adjusting until the correct resistance $R_S$ is reached to balance the bridge 208. In other words, when the resistance $R_2$ is changed, the temperature of the sensor 201 will change, by changing $V_A$, to match a new value required for resistance $R_S$. The temperature of the sensor 201 is thus set so as to accurately and reliably establish a stable, selectable, and predetermined temperature differential between the sensor 201 and the wall of the cavity 234.

It will be recognized that although processor 230 is shown as a single block, it may in alternative embodiments be subsumed into the measuring circuit 250. The processor 230 may further comprise a network and bus system, input/output (I/O) controllers, isolation devices, and other related electronic components for performing control, processing, and communication functions other than those described herein. The processor 230 and/or variable resistor 202 may be constructed from discrete and integrated circuit devices amenable to the practice of this invention, e.g., one or more active devices such as computers, microprocessors, microcontrollers, switches, logic gates, or any equivalent logic device capable of performing the functions described herein. The processor 230 may include random access memories and read-only memories in which information and programming can be stored and retrieved by known methods. The memory may be used for storage and retrieval of operating condition parameters (such as temperatures, temperature differentials, and resistance values).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A thermal conductivity detector for detecting the thermal conductivity of a sample fluid, comprising:

a cavity wall defining a cavity for receiving a quantity of the sample fluid, said cavity wall having a cavity wall temperature;

a sensor located in said cavity and connected as a first element in a bridge circuit configuration, said sensor having a sensor resistance which is dependent on a temperature of said sensor;

a selectable resistor having a selectable resistance in response to a resistor control signal, the selectable resistor being connected in said bridge circuit configuration as a second element wherein the resistance of said selectable resistor controls the temperature of said sensor;

signal providing means, connected to said sensor, for providing an output signal which is related to a change in the power delivered to said sensor and thereby representative of the thermal conductivity of the sample fluid;

heating means for providing a temperature sense signal representative of the cavity wall temperature and for controlling the cavity wall temperature in response to a heating control signal; and a controller connected to said selectable resistor and said heating means for;

a. receiving said temperature sense signal, b. determining a desired cavity wall temperature, a desired sensor temperature, and a respective temperature differential therebetween;

c. and in response, providing said heating control signal to effect said desired cavity wall temperature and providing the resistor control signal to effect the selected resistance of the selectable resistor so as to establish the desired temperature of the sensor;

whereby the desired temperature differential may be established between the temperature of the sensor and the temperature of the cavity wall.

2. The thermal conductivity detector of claim 1, wherein said signal providing means further comprises a differential amplifier connected to two balance nodes of said bridge circuit configuration for outputting an output signal based upon a voltage difference between said two nodes.

3. The thermal conductivity detector of claim 2, wherein said sensor further comprises: a resistive element having a resistance that changes in proportion to changes in a temperature of said element, said resistive element being heated by an electric current through said resistive element, said resistive element being contained in the cavity so that an equilibrium temperature of said resistive element is inversely proportional to a rate of heat transfer between said resistive element and the cavity wall.

4. The thermal conductivity detector of claim 3, wherein said bridge circuit configuration comprises: said selectable resistor having first and second terminals, said second terminal of said selectable resistor being connected to a first terminal of said resistive element; a second resistor having a first and second terminal, said first terminal of said second resistor being connected to said first terminal of said selectable resistor; a third resistor having a first and second terminal, said first terminal of said third resistor being connected to said second terminal of said second resistor, said second terminal of said third resistor being connected to a second terminal of said resistive element; and said differential amplifier having first and a second input voltage terminals, said first input voltage terminal being connected to said first terminal of said selectable resistor, said second input voltage terminal being connected to said second terminal of said resistive element.

5. The thermal conductivity detector of claim 1, further comprising means for measuring said output signal and in response, providing a signal indicating the relative presence of an analyte in the sample fluid.

6. The thermal conductivity detector of claim 1, wherein said controller further comprises an analog to digital converter for receiving said temperature sense signal and a processor for providing said temperature control signal and said resistor control signal.

7. A method for detecting the presence of an analyte in a sample fluid, comprising the steps of:

providing a cavity wall defining a cavity for receiving a quantity of the sample fluid, the cavity wall having a cavity wall temperature;

providing a sensor in the cavity, the sensor being operatively connected as a first element in a bridge circuit configuration, the sensor having a sensor resistance which is dependent on a sensor temperature;

providing a selectable resistor in the bridge circuit configuration as a second element wherein a selectable resistance of the selectable resistor controls the temperature of the sensor, the selectable resistance being selected in response to a resistor control signal;

operatively connecting a heating means to the cavity wall for providing a temperature sense signal representative of the cavity wall temperature and for controlling the cavity wall temperature in response to a heating control signal; and operatively connecting a controller to the selectable resistor and the heating means, the controller being operable for:

a) receiving the temperature sense signal, b) determining a desired cavity wall temperature, a desired sensor temperature, and a respective temperature differential therebetween;

c) in response to the determination in step (b), providing the heating control signal to effect the desired cavity wall temperature and providing the resistor control signal to effect the resistance of the selectable resistor so as to establish the temperature of the sensor; and connecting a signal providing means to the sensor for providing an output signal that is representative of the thermal conductivity of the sample fluid;

whereby the desired temperature differential may be established between the temperature of the sensor and the temperature of the cavity wall and whereby the presence of the analyte in the sample fluid may be detected according to said output signal.

\* \* \* \* \*